United States Patent [19]

Berthold et al.

[11] Patent Number: 5,290,513
[45] Date of Patent: Mar. 1, 1994

[54] RADIATION MEASURING DEVICE, PARTICULARLY FOR LUMINESCENCE MEASUREMENTS

[75] Inventors: Fritz Berthold, Pforzheim; Willy Lohr, Wildbad, both of Fed. Rep. of Germany

[73] Assignee: Laboratorium Prof. Dr. Rudolf Berthold GmbH & Co. KG, Wildbad, Fed. Rep. of Germany

[21] Appl. No.: 914,742

[22] Filed: Jul. 20, 1992

[30] Foreign Application Priority Data

Jul. 18, 1991 [DE] Fed. Rep. of Germany ....... 4123817

[51] Int. Cl.$^5$ ............................................. G01N 21/76
[52] U.S. Cl. ......................................... 422/52; 422/65; 422/82.05; 250/361 C; 356/246
[58] Field of Search ..................... 250/361 C; 356/244, 356/246; 436/172, 47; 422/52, 63, 64, 65, 67, 82.05, 82.08

[56] References Cited

U.S. PATENT DOCUMENTS

| | | | |
|---|---|---|---|
| 4,224,278 | 9/1980 | Hogen Esch | 422/65 |
| 4,267,149 | 5/1981 | Bruckner et al. | 422/65 |
| 4,451,433 | 5/1984 | Yamashita et al. | 422/65 X |
| 4,582,990 | 4/1986 | Stevens | 422/65 X |
| 4,586,818 | 5/1986 | Lohr | 356/244 |
| 4,772,453 | 9/1988 | Lisenbee | 422/52 |
| 4,985,631 | 1/1991 | Wannlund et al. | 422/52 X |
| 5,048,957 | 9/1991 | Berthold et al. | 250/361 C X |
| 5,104,621 | 4/1992 | Pfost et al. | 422/65 X |
| 5,169,601 | 12/1992 | Ohta et al. | 422/82.08 X |

FOREIGN PATENT DOCUMENTS

| | | |
|---|---|---|
| 0025350 | 3/1981 | European Pat. Off. . |
| 0181060 | 5/1986 | European Pat. Off. . |
| 3110239 | 10/1982 | Fed. Rep. of Germany . |
| 2207245 | 1/1989 | United Kingdom . |

OTHER PUBLICATIONS

"Microplate Lumino meter LB 96 P" by Berthold.

*Primary Examiner*—James C. Housel
*Assistant Examiner*—Jeffrey R. Snay
*Attorney, Agent, or Firm*—Spensley Horn Jubas & Lubitz

[57] ABSTRACT

A radiation measuring apparatus for performing measurements on samples contained in a plurality of sample containers disposed in the form of a matrix on a holder plate, the apparatus including a radiation detector having an entrance window, displacement devices for aligning successive sample containers with the entrance window of the radiation detector for automatic measurement of samples in the sample containers, the radiation detector and the sample containers being movable relative to one another in such a way that the sample container being measured and the entrance window of the detector are disposed coaxially with each other. The apparatus further includes: a diaphragm plate (10) provided with at least one aperture, the diaphragm plate being fixedly disposed between the entrance window (31) of the detector (30) and a sample container (21) placed underneath the entrance window; a component forming a light-tight coupling between a sample container (21) placed underneath the entrance window and the entrance window; and a component disposed for pressing the sample containers against the diaphragm plate (10) with a constant pressure while permitting the sample containers to be displaced parallel to the diaphragm plate by the displacement devices.

21 Claims, 4 Drawing Sheets

RADIATION MEASURING DEVICE, PARTICULARLY FOR LUMINESCENCE MEASUREMENTS

FIELD OF THE INVENTION

The invention relates to a radiation measuring device, particularly for luminescence measuring, having displacing devices for the successive assignment of a particular sample container to the entrance window of a radiation detector for automatic measuring of a plurality of sample containers disposed in the form of a matrix on a holder plate. The sample containers or the radiation detector are displaceable in such a way that, in the position of measurement of one sample container, this sample container and the entrance window of the detector are disposed coaxially with each other and are essentially placed on top of each other in a light-tight manner.

BACKGROUND OF THE INVENTION

A radiation measuring device for luminescence measuring is known, for example, from U.S. Pat. No. 4,772,453. The basic principle of the arrangement therein disclosed is a fixedly disposed radiation detector which successively receives luminescence signals from individual sample containers conducted underneath an entrance window and a reflection optical device, particularly as shown in FIG. 11 of that patent. In this case, $M \times N$ sample containers are located on a common holder plate which can be displaced in the x-y plane by means of suitable guide rods and associated drive elements in such a way that every single sample container on the holder plate comes to rest underneath the entrance window of the radiation detector. The displacing devices required for this take up a fairly large space and must be exactly aligned with each other so that the proper association between the sample container and the entrance window is achieved in a dependable manner and in exact steps for each of the sample containers. Therefore this plurality of guide elements, such as guide rails and guide sleeves sliding thereon, must be manufactured and assembled with high mechanical precision (or within correspondingly low tolerance limits) so as to somewhat assure this dependable association and also to reduce disruptions because of mutual obstruction of the x-y displacements, for example by tilting or binding, to a minimum.

Devices for additional vertical movements of the detector require that their movement paths be coordinated with the movement paths of the components responsible for the horizontal displacement of the recording plate in the x-y plane, which therefore leads to further structural complications.

Apparently the problems in regard to the known displacement devices have already been recognized; however, a solution was apparently seen (as also suggested in European Patent Disclosure EP-A-0 181 060) to lie in conceiving a measuring device with a plurality of detectors disposed in rows (European Patent Disclosure EP-A-0 025 350; German Published, Non-Examined Patent Application DE-OS 31 10 239) which, although it allows for a simpler, one-dimensional displacement of the sample holder, entails a disproportionately large expenditure for component parts. Thus, this prior art proposes a plurality of radiation detectors instead of a solution to the problems associated with a displacement device.

A comparison of the two mentioned references shows that the basically desirable properties of a structurally simple construction on the one hand and light-tight shielding of the critical connecting area between sample container and radiation detector in the measuring position, on the other, cannot be realized by means of the suggested solutions, or that at least no concrete way of accomplishing this is discernible from the prior art.

SUMMARY OF THE INVENTION

It is therefore an object of the invention to provide a radiation measuring device having a measuring sensitivity which is high and constant from sample to sample and in which, in the measuring position, the shielding of the luminescence signal against ambient light, such as crosstalk effects, is improved.

Another object of the invention is to provide such a device which satisfies the above somewhat competing requirements and yet operates in a simple and precise fashion.

The above and other objects are attained in accordance with the invention, in a radiation measuring device for performing measurements on samples contained in a plurality of sample containers disposed in the form of a matrix on a holder plate, the apparatus including a radiation detector having an entrance window, displacement units for aligning successive sample containers with the entrance window of the radiation detector for automatic measurement of samples in the sample containers, the radiation detector and the sample containers being movable relative to one another in such a way that the sample container being measured and the entrance window of the detector are disposed coaxially with each other, by the improvement wherein the device further comprises:

a diaphragm plate provided with at least one aperture, the diaphragm plate being fixedly disposed between the entrance window of the detector and a sample container placed underneath the entrance window;

means for forming a light-tight coupling between a sample container (21) placed underneath the entrance window and the entrance window; and means disposed for pressing the sample containers against the diaphragm plate (10) with a constant pressure while permitting the sample containers to be displaced parallel to the diaphragm plate by the displacement units.

In the first place, a basic premise of the solution in accordance with the invention involves mounting the diaphragm plate so that it is stationary and pressing the sample containers resiliently against the underside of the diaphragm plate, whereby optimum light shielding of the sample containers is made possible. In addition, this combination of features also fulfills an essential mechanical task: because of its stationary fixation, the diaphragm plate forms a "striking face" for the sample containers which are resiliently pressed against it from below. In turn, this striking function relieves the radiation detector seated from above on the diaphragm plate or an appropriate connecting element for the radiation detector of the responsibility for exerting pressure on the sample containers. In addition, the resilient pressure on the holder plate with the sample containers allows small rocking or tilting movements of the holder plate around horizontal axes; these movements automatically result in an automatic orientation of the holder plate containing the sample containers parallel to the stationary diaphragm plate. By means of this it is possible, for example, to compensate for possible fabrication inaccuracies in the height of the sample containers.

Thus, a first practical realization of the idea of the invention can consist in that the sample containers in their entirety are transported two-dimensionally in the x-y plane similar to the already known device, but that the described inaccuracies on account of vertical, small movement components which might be caused in the course of employment of displacement devices in accordance with, for example, U.S. Pat. No. 4,772,453, and which result in the unavoidable disadvantages in connection with the already known construction, are compensated in that the holder plate is resiliently pressed against the diaphragm plate in every position and thus is aligned parallel to it.

In a second practical realization, the diaphragm plate is provided with several holes forming a row of holes, and the radiation detector is embodied in such a way that it can be glidingly displaced over these holes.

In this preferred embodiment of the invention, the displacement of the sample containers can take place along only one coordinate (x) and the displacement of the entrance window of the detector over the row of holes, which for this purpose is disposed vertically, along the other coordinate (y). Thus, in this case the diaphragm plate is used not only as an optical shielding element and striking surface, but also as a guide for the entrance window of the detector.

In contrast to the displacement mechanism in the first embodiment having a displacement device in accordance with the species, in which the displacement forces in the x-direction as well as in the y-direction are superimposed, so to speak, on the holder plate for the sample containers, the drives in this embodiment are not connected, i.e. one drive elements acts on the entrance window of the detector or on the detector itself (y-direction), the other drive element acts on the holder plate with the sample containers (x-direction). In this way each one of the drive elements must have the precision required for exact association and functioning only in the displacement direction assigned to it and must be connected correspondingly rigidly and precisely with the component to be displaced, while variances and losses of tolerance in the respectively other direction are acceptable without question. On the one hand, this considerably simplifies the technical structure and, on the other, provides the structural prerequisites for maintaining optimum optical shielding at the place of measurement, because the resilient pressure which is effective there acts in the z-direction and, accordingly, is independent of the drive elements acting in the x- and y-directions, on the one hand and, on the other, is not affected in its actions by possible tolerance losses of the components with their drive elements. Limiting the drive and guide elements used in each case to the required precision in respect to only one coordinate results in simplifying manufacture and thus in cost savings, and increases the long-term reliability of the device.

In addition, the linear movement of the holder plate with the sample containers makes possible, by an appropriate sizing of the displacement path, a simple, for example carriage-like, placement and/or removal of holder plates underneath the stationary diaphragm plate. In turn, this simple placement and removal permits further simplification in that, for example, a plurality of holder plates can be placed in succession into the displacement plane by means of a paternoster-like feed device, positioned in the displacement plane and removed again on the other side fully automatically.

In accordance with an advantageous embodiment, the sample containers are embodied as wells in an integral or module-like designed sample plate (microtest or socalled microtiter plate), which is seated, fixed in the horizontal plane, on the holder plate, and that for resilient pressing, a resilient insert, for example offoamed material, is arranged, below the diaphragm plate, between the sample plate and the holder plate. However, for holding individual sample containers it is easily possible to use, for example, a separate holder block with appropriate receiving bores. In this case the sample container should be selected to be either transparent or opaque, depending on the type of luminescence reaction to be detected.

Here the holder plate can be simply adapted to the size of the various sample plates. The embodiment of the resilient insert of foamed material, for example as a strip of foamed material extending along the edge of the sample plate, is structurally simple, cost-effective and dependable.

In accordance with further advantageous embodiments, the bottom of the holder plate can be set at a vertical distance H in relation to the underside of the diaphragm plate, so that the resilient insert is compressed in the measuring position and therefore generates the force which presses the sample containers against the underside of the diaphragm plate.

The thickness of the foamed material insert as well as the magnitude of the distance H therefore define the pressure force with which the microtiter plate is pressed against the stationary diaphragm plate from below and by which the sample containers are shielded.

The edge of the diaphragm plate which faces opposite the displacement direction of the holder plate has a ramp-shaped slope, by means of which the resilient insert disposed in the holder plate is compressed. This ramp-shaped slope generates the compression of the foamed plastic insert required for the stated purposes when the holder plate with the sample plate is moved from a position away from the stationary diaphragm plate (for example in a loading and removal position) to its position beneath the diaphragm plate.

In further accordance with the invention, the guide elements on the top of the stationary diaphragm plate are constituted by the sides of a guide groove whose bottom contains the row of holes. This guide groove not only offers the advantage of a simple structural design and simple manufacture, but it furthermore has an additional shielding effect. This shielding effect is reinforced if, in accordance with a further embodiment, a guide block with a diaphragm bore is disposed to be slidingly displaceable in the guide groove and to enclose the entrance window of the detector in a light-tight manner.

A further improvement can be achieved if in accordance with another embodiment the length L of the guide block, in the direction parallel to the guide groove, is selected to be such that the guide block closes off at least the two adjoining holes of the row of holes when its diaphragm bore is aligned with a hole of the row of holes, this being the measuring position for the hole with which the bore is aligned. With this, any crosstalk effects by the two sample containers which adjoin in the direction of the guide groove are eliminated for all practical purposes.

According to another feature, a further, second row of holes is disposed parallel to the first-mentioned row of holes, to unblock the openings of the adjoining row of sample containers. By means of this it is possible to perform preparatory measurement steps, for example the addition of a luminescence-initiating substance, should this be desirable or necessary, and such addition need not take place simultaneously with or immediately prior to measuring.

Further, the diaphragm plate may extend beyond the holder plate in the direction of the guide groove and at least one of the holes of the row of holes may be located there. This additional hole is used as a standby position or end position of the associated drive element, or for test purposes, or for purging of supply lines, or priming. In this connection it is necessary as a rule to provide a receptacle below this additional hole.

For the structurally advantageous embodiment of the components for detecting luminescence, the entrance window is connected, in accordance with a further embodiment, with the input of the radiation detector, in particular a photomultiplier, via an optical-fiber light guide device which bend the path of travel of the radiation, or photons, to be measured through an angle of approximately 90° so that the radiation enters the photomultiplier while travelling along a horizontal path. The geometric layout of this arrangement can be approximately compared with that of the device disclosed in the above mentioned U.S. Pat. No. 4,772,453; however, guidance of the photons in an optical-fiber light guide is a technically better solution than the reflecting optical device therein described. In view of the mechanical concept of the arrangement in accordance with the invention, an opportunity is provided for embodying the entrance window, the optical-fiber light guide and the radiation detector in the form of a rigid component, and this component may be mounted to be pivotable around a first axis located parallel to the direction of displacement of the holder plate (x-direction).

Thus, the entrance window, or the guide block, is located in the guide groove, which is roughly comparable with the pick-up system of a phonograph, where the optical-fiber light guide and the radiation detector correspond to the tone arm.

In accordance with a further embodiment, the "stylus pressure" of the entrance window or the guide block in the guide groove can be defined in that a spring element acts on this rigid component of entrance window/optical-fiber light guide/radiation detector at a location separated from the first axis and generates a torque by which the guide block is pressed into the guide groove with a defined vertical force. The desired stylus force of the guide block on the guide groove can be generated by proper selection of this spring element as a function of the weight of the radiation detector and any other forces and weights acting on this lever arrangement, which on the one hand allows for trouble-free gliding in the guide groove and, on the other, is practically impervious to tolerance errors in the vertical plane (z-direction).

According to a further advantageous feature of the invention, the entrance window with the optical-fiber light guide is pivotable around a second axis coaxial with the longitudinal, optical, axis of the photomultiplier. This simple further feature permits easy inspection of the inlet cross section of the entrance window,
because the latter can be pivoted upward around this second axis Y—Y into the field of view of the user.

It is furthermore provided that an injecting device is supported above the entrance window, via which a chemical substance can be injected in the measuring position through the entrance window, the diaphragm bore of the guide block and one of the holes of the row of holes of the diaphragm plate into a sample container.

In contrast to known radiation measuring devices, this provides an opportunity to supply a luminescence-initiating substance with optimum shielding against scattered radiation, in particular from the outside, and to conduct the photons which occur immediately thereafter to the photomultiplier via the optical-fiber light guide. Measurements of this kind are impossible with the known radiation measuring devices.

Measurements at a given time after the addition of reagents is possible in a simple manner with the device of the invention in accordance with a further feature, in that a further injecting device is supported above the entrance window, via which a chemical substance can be injected through a hole of the second row of holes into a sample container.

An alternate embodiment provides that the radiation measuring device of the invention has an optical-fiber light guide in place of a further injecting device, through which fluorescence-exciting light is conducted into the sample chamber for performing fluorescence measurement. It is of course necessary that the optical-fiber light guide employed for this be permeable to the short-wave light often required for fluorescence measuring, so that it is preferably made of quartz.

Further embodiments of the invention relate to the design of the housing of the radiation measuring device of the invention, where a loading and unloading opening is of particular importance, through which the sample plates are inserted and removed and which can be closed off in a light-tight manner by means of a lid. During the performance of the measurements a security lock comes into action and prevents the opening of this lid.

An exemplary embodiment of the radiation measuring device in accordance with the invention will be described in detail, with reference to the drawings.

DESCRIPTION OF THE PREFERRED EMBODIMENTS

Figure 1:
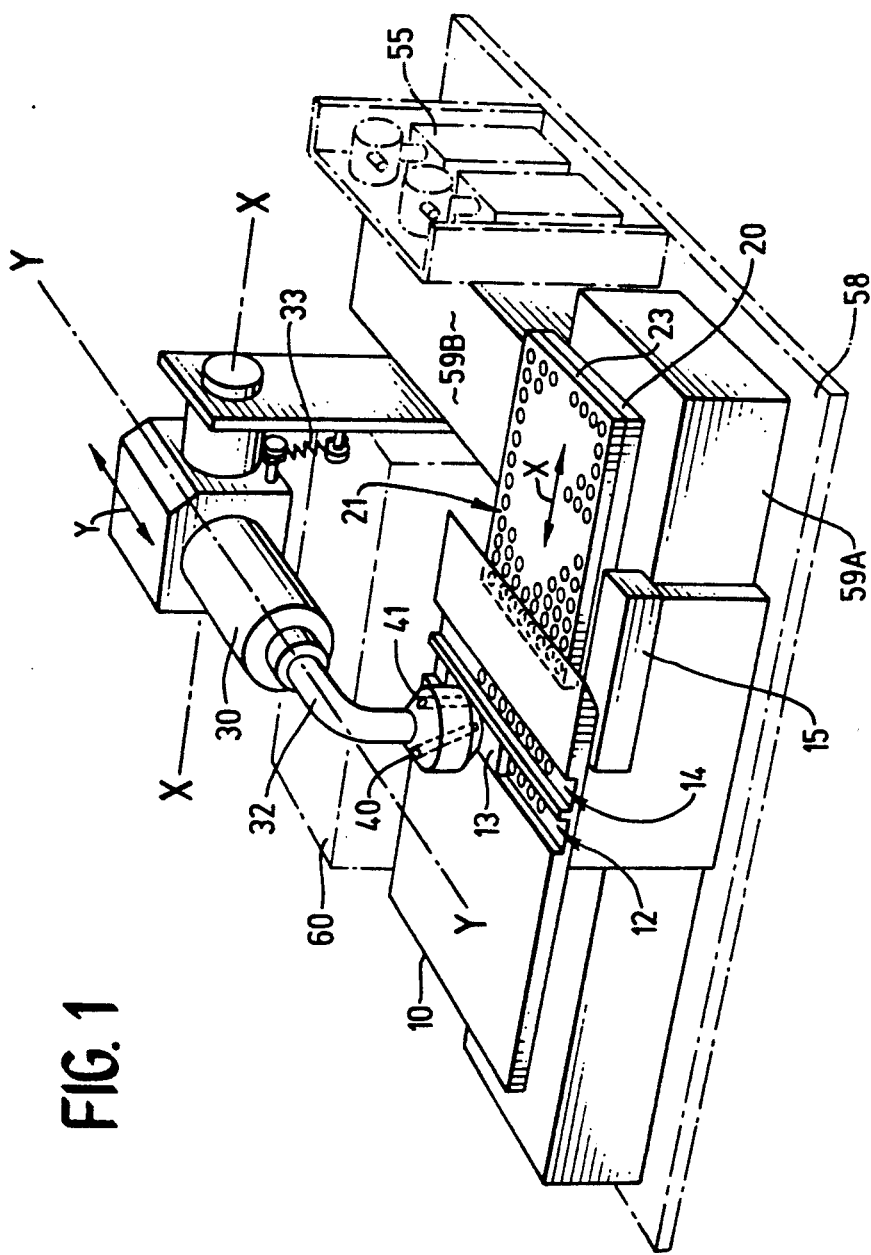
FIG. 1 is a perspective, simplified view of a radiation measuring device according to a preferred embodiment of the invention with its housing removed.

FIG. 1 shows a preferred embodiment of the radiation measuring device according to the invention in a perspective view (without the housing, illustrated separately in FIG. 4) and, to simplify the view, without hose and line connections, such as the electrical supply connections for the photo-multiplier 30, in particular, or hose connections from the injector pump block 55 to the injecting devices 40, 41.

The illustrated radiation measuring device is composed of a plurality of essential components which are mounted on a base plate 58. One of these components is a stationary diaphragm plate 10, consisting of an opaque material (plastic or metal) fixedly disposed above, and lying parallel to base place 58. A first drive block 59A is disposed underneath diaphragm plate 10. Drive block 59A is frictionally connected or connectable with a holder plate 20 which is provided to support a sample plate 23 that carries sample containers 21. Sample plate 23 is, for example, a microtiter plate. Drive block 59A has drive elements, such as a spindle drive or toothed belt arrangements as disclosed in the above cited U.S. patent, for displacing holder plate 20 in the x-direction from a first end position, shown in FIG. 1, at least as far as a second end position in which the last row of sample containers to the right in FIG. 1 is in the measuring position below the stationary diaphragm plate 10. A read-out device 15 is fixed on the housing of drive block 59 to detect a bar code on a lateral surface of sample plate 23 which faces device 15.

A second drive block 59B is connected with a device composed of a detector 30, a optical-fiber light guide 32 and an entrance window 31 in such a way that the entire device 30–32 is horizontally displaceable in the y-direction, so that entrance window 31 can glide in a guide groove 12 cut into the stationary diaphragm plate 10 also in the y-direction. The displacement path in the y-direction generated by the drive block 59B is here defined in such a way that the two end positions of entrance window 31 at least cover the two outermost bores of a row of holes 11, where the entrance window 31 is seated firmly in a guide block 13, which is displaceable in the guide groove 12 in the y-direction, in such a manner that extraneous light is prevented from entering light guide 32. Guide block 13 has a hole 13A through which a respective one of the row of holes 11, and thus an associated sample container 21, are placed in optical communication with light guide 32.

The entire device composed of detector 30, optical-fiber light guide 32 and guide block 13 is pivotable around a horizontal axis X—X (in the x-direction), so that guide block 13 follows the path of guide groove 12 approximately comparable to the manner of a pick-up stylus in a phonograph. A spring element 33, which acts on this component at a connection point spaced laterally from the pivot axis X—X, generates a definable torque which results in a defined vertical force of the guide block 13 in the guide groove 12. In this case this torque counteracts torques created by connector elements, such as cables or the like, on the detector 30, so that the effect of these connector elements on the vertical force of the guide block 13 can be assuredly compensated.

The optical-fiber light guide 32 with the entrance window 31 and the guide block 13 is also pivotable around a pivot axis Y—Y (in the y-direction) located coaxially to the detector 30. By means of the combination of these two pivot movements it is for example easily possible to check the entrance window 31 with the optical-fiber light guide 32 which terminates there by first pivoting the entire component upwards around the axis X—X and then pivoting the optical-fiber light guide away around the axis Y—Y.

An injector pump block 55 is located along one side of base plate 58. Pump block 50 has two connectors which are connected with injecting devices 40, 41 by means of pump hoses (not shown).

A further row of holes 14 is located parallel to the row of holes 12 and their purpose will be explained herein below.

Finally, an electronic unit 60 is housed on the base plate 58. Unit 60 is responsible for evaluating the signals of detector 30 in coordination with the position of holder 23 and detector 30, and is controlled via an operating and display panel 51 (FIG. 4) in the housing. Unit 60 is connected with drive blocks 59A and 59B via appropriate control lines.

Before the mode of operation of the radiation measuring device is explained, details in the area of the stationary diaphragm plate 10 will be described with reference to the sectional views of FIGS. 2 and 3.

Figure 2:
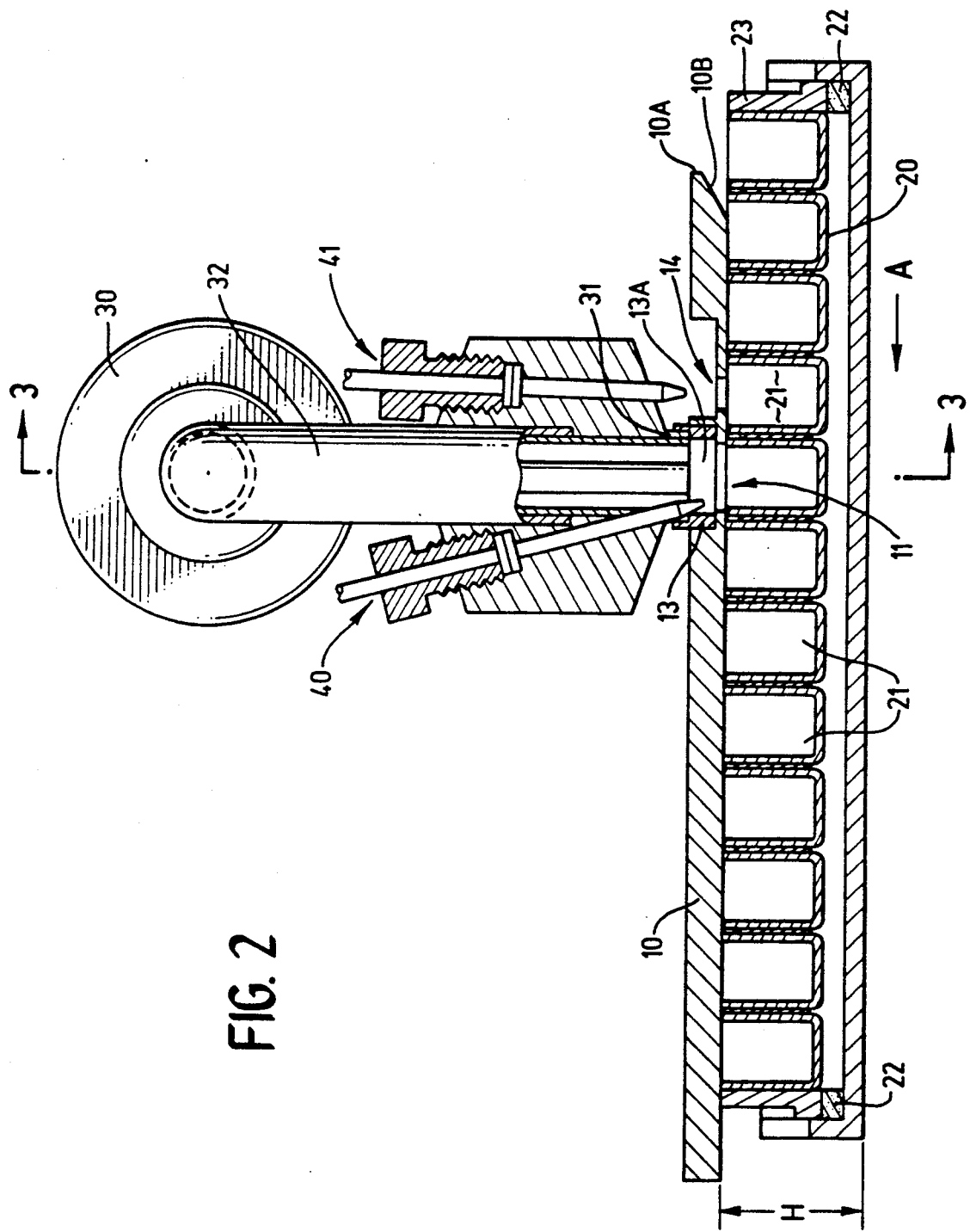
FIG. 2 is a cross sectional taken view in the x-z plane II—II of FIG. 3.
Figure 3:
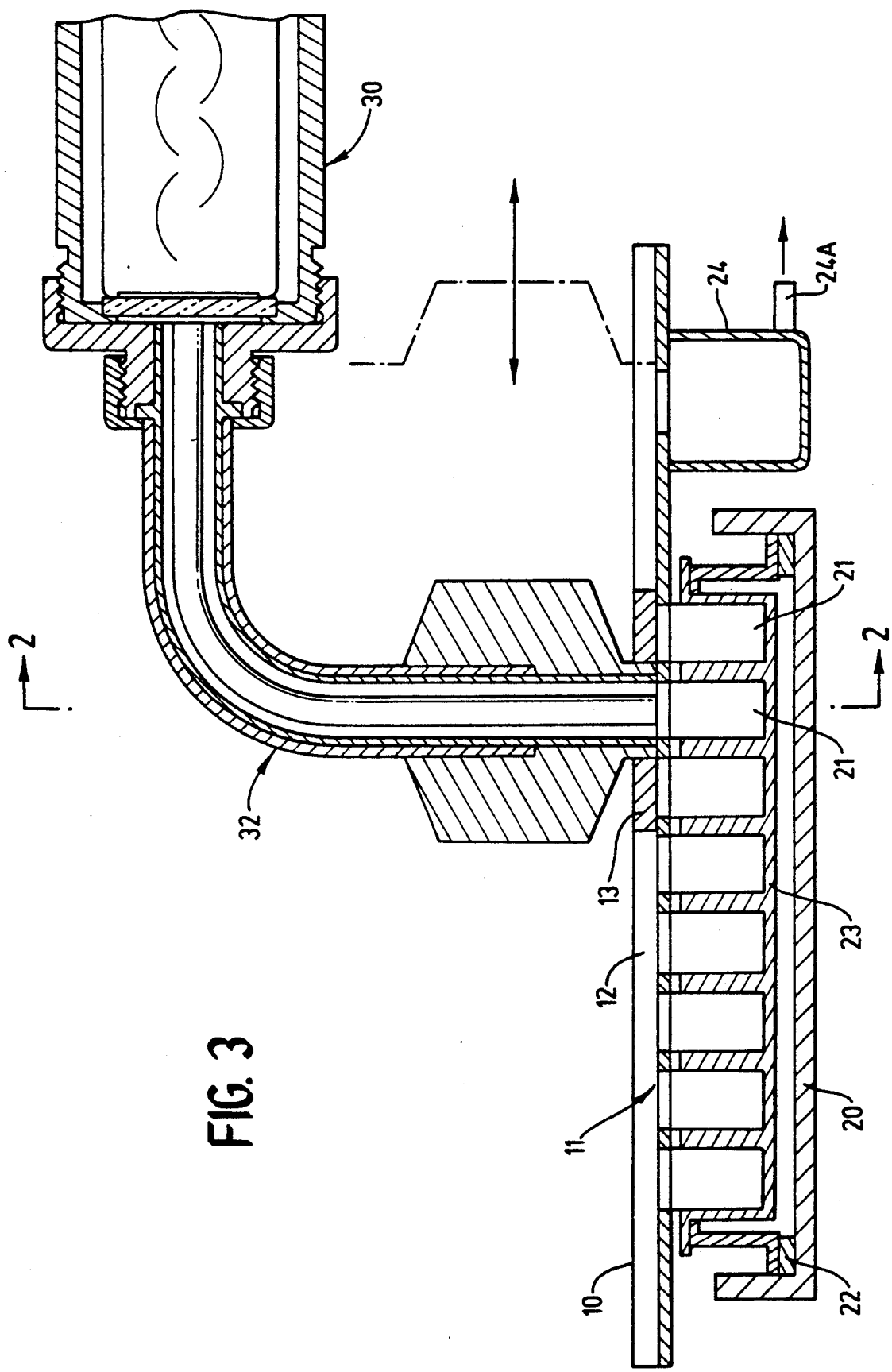
FIG. 3 is a second sectional view in the y-z plane III—III of FIG. 2.

In FIGS. 2 and 3 the holder plate 20 with the sample plate 23 carrying sample containers 21 is located underneath the diaphragm plate 10. Between the holder plate 20, embodied in the shape of a tub, and the underside of the sample plate 23, a foamed material strip 22 is inserted, along edge of sample plate 23. Foamed strip 22 is compressed in the position illustrated, so that the sample containers 21 are firmly pressed against the underside of the diaphragm plate 10 in that the upper edges of containers 21 contact the underside of diaphragm plate 10. Optical shielding is provided, as illustrated without a reference numeral, between adjoining sample containers to prevent light crosstalk effects between adjacent containers 21.

The front edge 10A of diaphragm plate 10, shown on the right in FIG. 2, has a ramp-shaped slope 10B which, when the sample plate 23 is moved from the front end position illustrated in FIG. 1, into the measuring position illustrated in FIG. 2, causes the sample plate 23 to be pressed against the underside of the diaphragm plate 10 during insertion movement (arrow A in FIG. 2), while the foamed material strip 22 is being compressed.

In connection with the preferred employment of a so-called microtest plate ("microtiter" plate) as a sample plate 23 with integrated, i.e. one-piece or modularly constructed, sample containers 21, such a sample plate 23 contains eight x twelve sample containers 21 (12 in the x-direction in FIG. 2, 8 in the y-direction in FIG. 3).

The row of holes 11 formed in diaphragm plate 10 is of such a size that the holes are congruent with the openings of a row of sample containers 21, as can be seen from FIG. 3 in particular. This row of holes is located in the bottom of the guide groove 12, in which the guide block 13 glides in a freely displaceable manner. Entrance window 31 of optical-fiber light guide 32 terminates at guide block 13. In the preferred embodiment shown, the guide block 13 is embodied as an elongated cuboid, or a plate with a rectangular outline, provided at its center with a diaphragm bore 13A which is slightly larger than the holes of the row of holes 11 and the outlet openings of the sample containers 21.

The cooperation of the above described elements thus makes it possible that by displacing the guide block 13 in the guide groove 12 (displacement of the component 30/32/13 by means of the drive block 59B), the opening of a sample container 21 is always exactly unblocked. This means that the detector 30 can "look", via the optical-fiber light guide 32, the diaphragm bore 13A and the hole of the row of holes 11 located underneath it, into the sample container centered below diaphragm bore 13A.

In the exemplary embodiment shown, a first injecting device 40 terminates in the diaphragm bore 13A of the guide block 13, by means of which, particularly during chemical luminescence measurements, a chemical substance which initiates the luminescence reaction can be injected into the sample container 21 located underneath diaphragm bore 13A when the measuring position has been attained. After this, the immediately occurring luminescence photons are detected in a known manner by the detector 30 via the optical-fiber light guide 32, are associated with this individual sample container by the electronic unit 60 and are appropriately stored.

A further injecting device 41 is provided to make it alternatively or additionally possible to inject chemical substances in the adjoining row of sample containers 21 through the openings of a second row of holes 14 for measurements of various types. This is also provided, for example, in connection with the radiation measuring device in accordance with the species represented by this embodiment, where such an injecting device is used for injecting the luminescence-activating substance.

Although the described embodiment of the structural design and the association of the detector/optical-fiber light guide/entrance window and injecting devices is particularly advantageous, it is stressed that it is basically unimportant for the operation of the radiation measuring device in which way the photons coming through the diaphragm bore 13A of the guide block 13 are finally generated and/or evaluated. For example, arrangements in accordance with the radiation measuring device of the species of the described embodiment are conceivable for this, or there can be direct coupling with a detector, for example, in which case the entrance window 31 would be formed by the entrance window of the detector directly or via an additional component. In the preferred exemplary embodiment illustrated it is particularly advantageous (FIG. 3), if the diaphragm plate 10 laterally extends beyond the holder plate 20 and if a further hole with a receptacle 24 and a draw-off connector 24A underneath it are provided alongside plate 20. The position which the diaphragm bore 13A takes up over this receptacle 24 would then be the end position (partially indicated by dashed lines in FIG. 3) of the evaluation unit consisting of the detector 30 and the optical-fiber light guide 32. In this position, which can constitute a "priming position", it is possible in a particularly preferable manner to perform purging and testing operations with the aid of the injecting devices 40 and 41.

Figure 4:
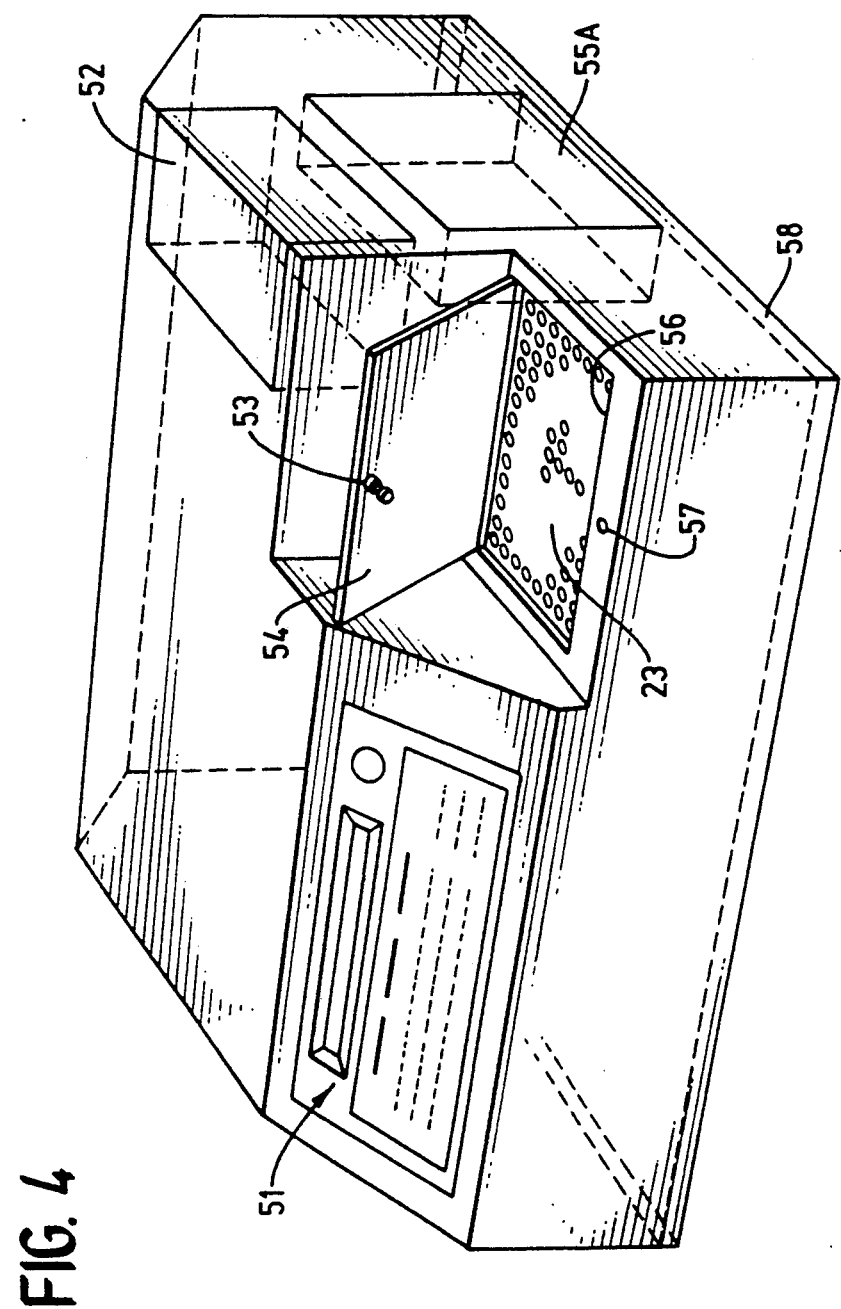
FIG. 4 is a perspective view illustrating the housing of a device according to the invention.

The housing 50, shown in FIG. 4, is used to enclose the entire radiation measuring device in a light-tight manner.

An operating and display panel 51 is used for controlling the radiation measuring device and to display operational states and measured values. A receptacle chamber 52 is used for the secure storage of the chemical reagents required. A lateral recess 55A is provided for housing the injector pump block 55 and a loading and unloading opening 56 is provided for inserting and removing a sample plate 23 with sample containers 21 (for example a microtiter plate). This loading and unloading opening 56 can be closed off in a light-tight manner with a lid 54 and corresponding latching elements 53/57, which engage each other and assure that the lid 54 can only be opened when the sample plate 23 with the sample containers 21 is in the end position shown in FIG. 4, i.e. not in the measurement position.

The mode of operation of the radiation measuring device will now be briefly described by way of example:

After inserting the sample plate 23 in the loading and unloading opening 56, the lid 54 in the housing 50 is closed. Then the drive block 59A is activated and the lid 54 is simultaneously locked, so that access to the loading and unloading opening 56 is no longer possible.

Then the sample plate 23 with the sample containers 21 is pushed underneath the diaphragm plate 10 in the direction designated in FIG. 2 by A (x-coordinate), in the course of which the foamed material insert 22 is compressed and in this way the sample containers are pressed against the diaphragm plate 10 from below. As soon as the first row (the left one in FIG. 1) has been positioned (in the y-direction) below the row of holes 11 so that the holes of the row of holes 11 agree coaxially with the openings of the row of sample containers located below it, the advance of the drive block 59A is stopped and the first measurement is performed. Then the drive block 59A is again activated and in this way one row of twelve measuring positions, for example the rear row in FIG. 1, is traversed, with the detector 30 remaining stationary.

A suitable substance will be injected via the injecting device 40 in each one of these twelve measuring positions into the sample container 21 respectively located underneath, and the subsequent luminescence reaction will be measured by the detector 30 and registered by the electronic unit 60 (and possibly displayed at the operating and display panel).

After performing the first measuring sequence of twelve measurements, the holder plate 20 is pushed back opposite the direction A and the entrance window 31 with the guide block 13 of the detector 30 is advanced by one hole of the row of holes 11, so that the next row of sample containers can be measured, in the course of which again twelve measurements are performed.

Measurements are performed in this manner on $m=8$ (FIG. 3) rows of sample containers. After completing the measurements on $m \times n$ sample containers 21, the drive block 59A returns the holder plate 20 back into its end position below the loading and unloading opening 56. Upon reaching this position, the closing elements 53/57 are unlocked, so that the lid 54 can be opened and the sample plate 20 with the measured samples can be removed.

Further details of the injecting devices and the element carrying those devices are disclosed in a copending application Ser. No. 914,741 entitled RADIATION MEASURING DEVICE, IN PARTICULAR FOR LUMINESCENCE MEASUREMENTS, claiming priority of German application no. P 41 23 818.4-52 and filed on Jul. 20, 1992.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. In a radiation measuring device for performing measurements on samples contained in a plurality of sample containers, the apparatus including a radiation detector having an entrance window, sample container holding means defining a sample container holding region for holding a plurality of sample containers in a matrix pattern, and displacement devices for displacing the sample container holding means in order to align successive sample containers with the entrance window of the radiation detector for automatic measurement of samples in the sample containers, the radiation detector and the sample container holding means being movable relative to one another in such a way that the sample container being measured and the entrance window of the detector are disposed coaxially with each other, the improvement wherein said device further comprises:

a diaphragm plate (10) provided with at least one aperture, said diaphragm plate being fixedly disposed between said aperture, said diaphragm plate being fixedly disposed between said entrance window (31) of said detector (30) and said sample container holding region;

means for forming a light-tight coupling between a sample container (21) placed underneath said entrance window and said entrance window; and means disposed for pressing the sample containers against said diaphragm plate (10) with a constant pressure while permitting the sample containers to be displaced parallel to said diaphragm plate by said displacement devices.

2. A radiation measuring device in accordance with claim 1, wherein said entrance window of said detector is disposed above one aperture of said diaphragm plate (10).

3. A radiation measuring device in accordance with claim 1, in combination with a sample plate (23) having a lateral surface provided with a bar code and, said sample plate (23) having a plurality of sample containers (21) disposed in a horizontal plane, and a stationary read-out device (15) disposed alongside said sample plate (23) to detect the bar code, and wherein said sample container holding means comprise a holder plate on which said sample plate is mounted.

4. A radiation measuring device in accordance with claim 1, further comprising a light-tight housing (50) having a loading and unloading opening (56) via which sample containers (21) are inserted into and removed from said device, a lid (54) for closing the loading and unloading opening (56) in a light-tight manner, and a security lock (53, 57) for permitting access to the loading and unloading opening (56) only when sample containers which have previously been inserted into said device are located beneath the loading and unloading opening (56).

5. A radiation measuring device in accordance with claim 1, in combination with a sample plate (23) having a plurality of sample containers (21) disposed in a horizontal plane, wherein: said sample container holding means comprise a holder plate (20), said sample plate (23) being mounted on said holder plate (20).

6. A radiation measuring device in accordance with claim 5, wherein said diaphragm plate (10) has a horizontal orientation and a lower major surface, and said means for pressing the sample containers comprise a resilient insert (22) inserted between said sample plate (23) and said holder plate (20) for resiliently pressing said sample containers (21) against the lower major surface of said diaphragm plate (10).

7. A radiation measuring device in accordance with claim 6, wherein said holder plate (20) has a bottom disposed at a vertical distance (H) from the lower major surface of said diaphragm plate (10), the vertical distance (H) being selected such that in a measuring position of said holder plate (20), said resilient insert (22) is compressed and generates a pressure to press said sample containers (21) against the lower major surface of said diaphragm plate (10).

8. A radiation measuring device in accordance with claim 1, wherein said radiation detector comprises radiation detecting means (30) having a radiation input and an optical-fiber light guide device (32) coupling said entrance window (31) with said input of said radiation detecting means (30), said light guide device (32) providing a light guiding path which has a 90° bend between said entrance window and said radiation input of said radiation detecting means (30).

9. A radiation measuring device in accordance with claim 8, wherein said sample container holding means comprise a holder plate which is displaceable relative to said diaphragm plate along a first linear path (x) parallel to said diaphragm plate, and said entrance window (31), said light guide device (32) and said radiation detecting means (30) together constitute a rigid component which is pivotable around a first axis that extends parallel to the first linear path.

10. A radiation measuring device in accordance with claim 15, wherein said means for forming a light-tight coupling comprise a guide block (13) provided with a bore (13A), said guide block (13) being slidingly displaceable along said diaphragm plate (10) and enclosing said entrance window (31) of said detector (30) in a light-tight manner, and said device further comprises a spring element (33) connected to act on said rigid component (30, 31, 32) at a location separated from the first axis and to generate a torque by which said guide block (13) is pressed against said diaphragm plate (10) with a defined vertical force.

11. A radiation measuring device in accordance with claim 9, wherein said radiation detecting means have an optical axis and said entrance window (31) with said light guide device (32) is pivotable around a second axis aligned with the optical axis of said radiation detecting means (30).

12. A radiation measuring device in accordance with claim 9, wherein said means for forming a light-tight coupling comprise a guide block (13) provided with a bore (13A), said guide block (13) being slidingly displaceable along said diaphragm plate (10) and enclosing said entrance window (31) of said detector (30) in a light-tight manner, and said device further comprises an injecting device (40), supported above said entrance window (31), for injecting a chemical substance through said entrance window (31), said diaphragm bore (13A) of said guide block (13) and said at least one aperture of said diaphragm plate (10) into a sample container (21).

13. A radiation measuring device in accordance with claim 9, wherein said diaphragm plate (10) has a first plurality of apertures arranged in a row to form a first row of holes (11), over which said entrance window (31) of said detector (30) can be slidingly displaced, and a second plurality of apertures arranged in a row to form a second row of holes disposed parallel to said first row of holes (11), said second plurality of apertures being positioned to be disposed above one row of sample containers (21) when said first row of holes (11) is positioned to be disposed above a row of sample containers (21) which is adjacent the one row of sample containers (21), and said device further comprises an injecting device (41) supported above said entrance window (31) for injecting a chemical substance through a hole of the second row of holes (14) into a sample container (21).

14. A radiation measuring device in accordance with claim 1, wherein said diaphragm plate (10) has a plurality of apertures arranged in a row to form a first row of holes (11), over which said entrance window (31) of said detector (30) is capable of being slidingly displaced, and said diaphragm plate has guide elements for guiding said entrance window during displacement of said entrance window over said first row of holes.

15. A radiation measuring device in accordance with claim 14, wherein said displacement devices include means for displacing the sample container holding means along only a first linear path (x) parallel to said diaphragm plate and means for displacing said entrance window (31) of said detector (30) along only a second linear path (y), parallel to said diaphragm plate (10) and perpendicular to the first path (x) over the first row of holes (11), and said first row of holes extend parallel the second path (y).

16. A radiation measuring device in accordance with claim 15, wherein said diaphragm plate has a second plurality of apertures arranged in a row to form a second row of holes disposed parallel to said first row of holes (11), said second plurality of apertures being positioned to be disposed above one row of sample containers (21) when said first row of holes (11) is positioned to be disposed above a row of sample containers (21) which is adjacent the one row of sample containers (21).

17. A radiation measuring device in accordance with claim 15, in combination with a sample plate (23) having a plurality of sample containers (21) disposed in a horizontal plane, wherein: said sample container holding means comprise a holder plate (20), said sample plate (23) being mounted on said holder plate (20); said means for pressing the sample container comprise a resilient insert (22) inserted between said sample plate (23) and said holder plate (20) for resiliently pressing said sample containers (21) against said diaphragm plate (10); said holder plate is displaceable along the first linear path (x) in a displacement direction (A) into a measuring position; and said diaphragm plate (10) has a front edge (10A) which faces opposite the displacement direction (A) and which has a ramp-shaped sloping surface (10B) which acts to compress said resilient insert (22) as said holder plate (20) is displaced in the displacement direction (A).

18. A radiation measuring device in accordance with claim 15, wherein said diaphragm plate (10) has an upper major surface which faces away from the sample container holding region, and said guide elements are located at said upper major surface of said diaphragm plate (10) and are constituted by a guide groove (12) which contains said first row of holes (11).

19. A radiation measuring device in accordance with claim 18, wherein said means for forming a light-tight coupling comprise a guide block (13) provided with a bore (13A), said guide block (13) being slidingly displaceable in said guide groove (12) and enclosing said entrance window (31) of said detector (30) in a light-tight manner.

20. A radiation measuring device in accordance with claim 19, wherein said guide block (13) has a length in the direction of the second linear path (y) selected such that when said bore (13A) is located coaxially to one hole of said first row of holes (11), said guide block (13) closes off at least the two holes of said first row of holes (11) which adjoin the one hole.

21. A radiation measuring device in accordance with claim 20, wherein said diaphragm plate (10) extends beyond the sample container holding region in the direction of said guide groove (12), and at least one hole of said first row of holes (11) is located beyond the sample container holding region.

* * * * *